(12) United States Patent
Kuslich et al.

(10) Patent No.: US 6,383,188 B2
(45) Date of Patent: May 7, 2002

(54) EXPANDABLE REAMER

(75) Inventors: Stephen D. Kuslich, Stillwater, MN (US); Francis Peterson, Prescott; Todd Bjork, River Falls, both of WI (US); Joseph E. Gleason, Eagan, MN (US); Rodney Rogstad, Baldwin, WI (US)

(73) Assignee: The Spineology Group LLC, Stillwater, MN (US)

( * ) Notice: Subject to any disclaimer, the term of this patent is extended or adjusted under 35 U.S.C. 154(b) by 0 days.

(21) Appl. No.: 09/782,176

(22) Filed: Feb. 13, 2001

Related U.S. Application Data

(60) Provisional application No. 60/182,610, filed on Feb. 15, 2000.

(51) Int. Cl.$^7$ .............................................. A61B 17/56
(52) U.S. Cl. ........................................ 606/80; 408/158
(58) Field of Search .................... 606/80, 79, 81, 606/82, 84, 85; 408/157, 158, 154, 147, 161

(56) References Cited

U.S. PATENT DOCUMENTS

| | | | |
|---|---|---|---|
| 3,702,611 A | * | 11/1972 | Fishbein ..................... 408/157 |
| 5,002,546 A | * | 3/1991 | Romano ....................... 606/80 |
| 5,445,639 A | | 8/1995 | Kuslich et al. |
| 5,549,679 A | | 8/1996 | Kuslich |
| 5,571,189 A | | 11/1996 | Kuslich |
| 5,591,170 A | | 1/1997 | Spievack et al. |
| 5,667,509 A | * | 9/1997 | Westin ........................ 606/80 |
| 5,853,054 A | * | 12/1998 | McGarian et al. .......... 175/267 |
| 5,928,239 A | | 7/1999 | Mirza |
| 6,224,604 B1 | * | 5/2001 | Suddaby ...................... 606/80 |

* cited by examiner

*Primary Examiner*—Pedro Philogene
(74) *Attorney, Agent, or Firm*—Vidas, Arrett & Steinkraus, P.A.

(57) ABSTRACT

An expandable reamer for forming a space within a vertebral disc includes a pair of opposing blades which have a expanded state and a retracted state. The blades being pivotally positioned at the distal end of a shaft assembly. A shaft housing being substantially disposed about the shaft assembly. The proximal end of the shaft assembly being operatively engaged by a control device which when rotated allows the blades to be fully retracted for insertion into a pre-bored hole and then to be expanded incrementally until the cavity is bored as desired.

14 Claims, 12 Drawing Sheets

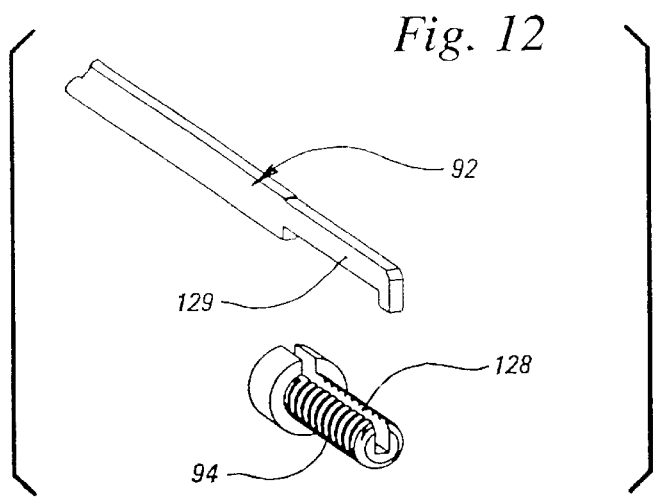
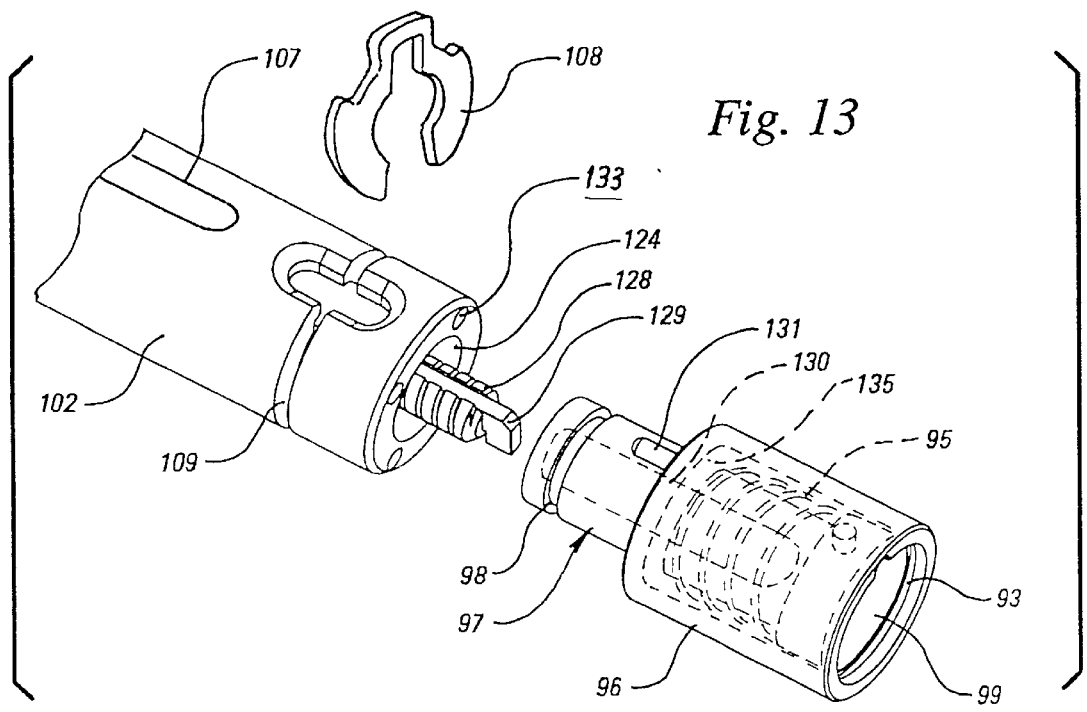

EXPANDABLE REAMER

CROSS-REFERENCE TO RELATED APPLICATIONS

The present Utility Patent Application claims priority to Provisional Application No. 60/182,610 filed Feb. 15, 2000, the entire contents of which being incorporated herein by reference.

STATEMENT REGARDING FEDERALLY SPONSORED RESEARCH

Not Applicable

BACKGROUND OF THE INVENTION

1. Field of the Invention

This invention relates to an expandable reamer for use in surgery, particularly in orthopedic applications.

2. Description of the Related Art

U.S. Pat. No. 5,445,639 to Kuslich et al., describes an intervertebral reamer which is used to ream out the interior of a degenerated disc to clean the interbody space. U.S. Pat. Nos. 5,549,679 and 5,571,189 to Kuslich describes a device and method for stabilizing the spinal segment with an expandable, porous fabric implant for insertion into the interior of a reamed out disc which is packed with material to facilitate bony fusion.

U.S. Pat. No. 5,928,239 to Mirza discloses a reamer which has a shaft and a cutting tip attached through a free rotating hinge such that high speed rotation allows the tip to be deflected outwardly to form a cavity. U.S. Pat. No. 5,591,170 to Spievack et al discloses a powered bone saw which inserts its cutting blade through a bored intramedullary canal.

The reamer of U.S. Pat. No. 5,445,639 is better suited to make a cylindrical bore than a spherical bore as is needed for the methods and apparatus of U.S. Pat. Nos. 5,549,679 and 5,571,189, the disclosure of all of which are incorporated herein by reference. There exists, therefore, a need for an instrument which will simplify the surgeon's task of forming a chamber within the interbody space.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

The invention provides a surgical tool is for forming hollow chambers within bone that are larger in diameter than the external opening into the chamber. The tool has a distal end with external dimensions sized to be passed through the patient's anatomy to a point of entry into the bone. Retractable cutting blades are provided on the cutting end. The blades can be extended to cut a cavity greater than the diameter of the surgical tool.

BRIEF DESCRIPTION OF THE DRAWINGS

A detailed description of the invention is hereafter described with specific reference being made to the drawings in which:

FIG. 12 is a close up view of threaded portion and end of the shaft shown in FIG. 11;

FIG. 13 is a view depicting the assembly of the barrel and turn wheel of the reamer shown in FIG. 11;

DESCRIPTION OF THE PREFERRED EMBODIMENTS

Reference is now directed to FIGS. 1 through 17 in which identical elements are numbered identically throughout.

Figure 1:
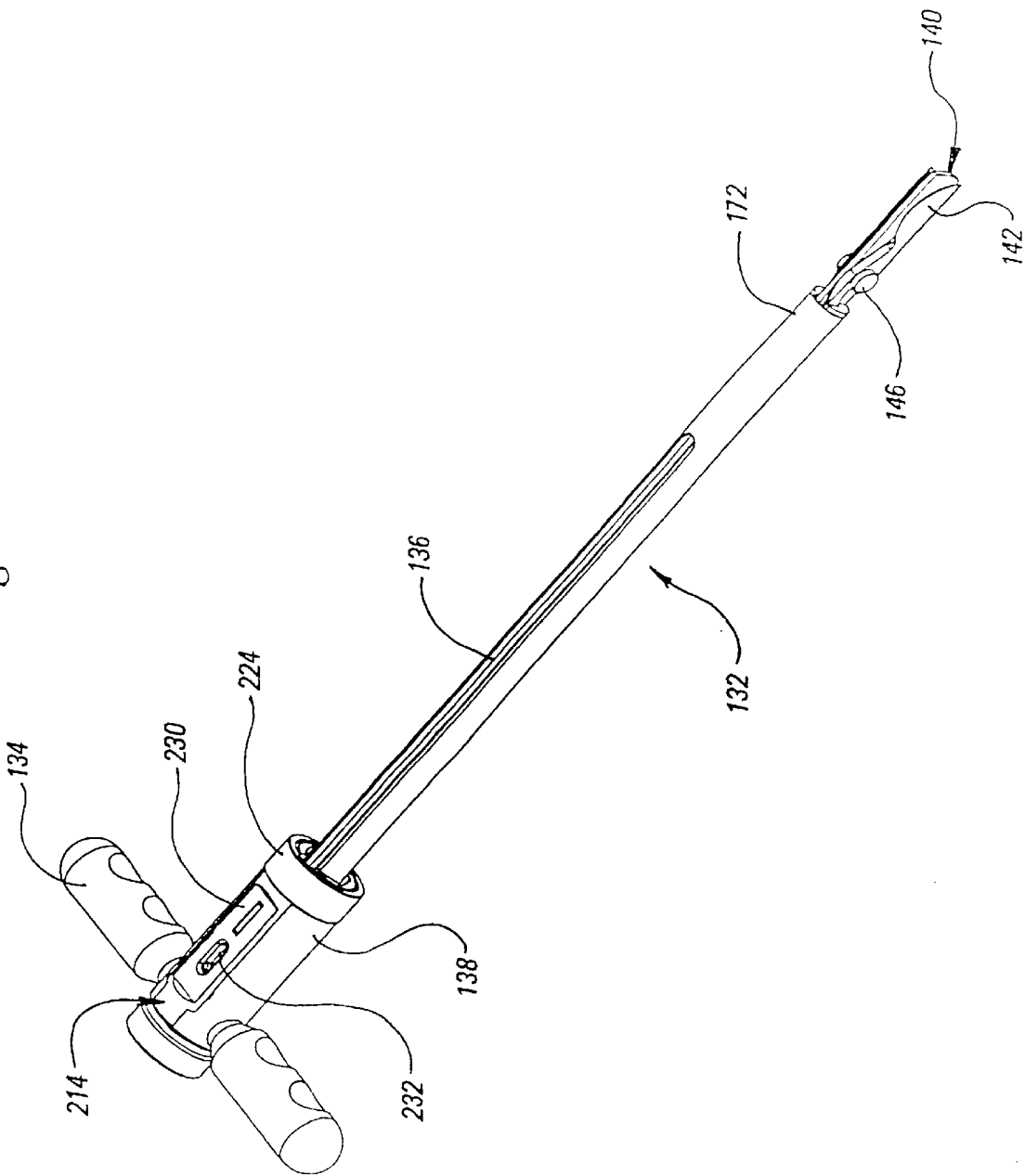
FIG. 1 is a perspective view of the reamer of the invention wherein the blades of the reamer are shown in the retracted position.
Figure 2:
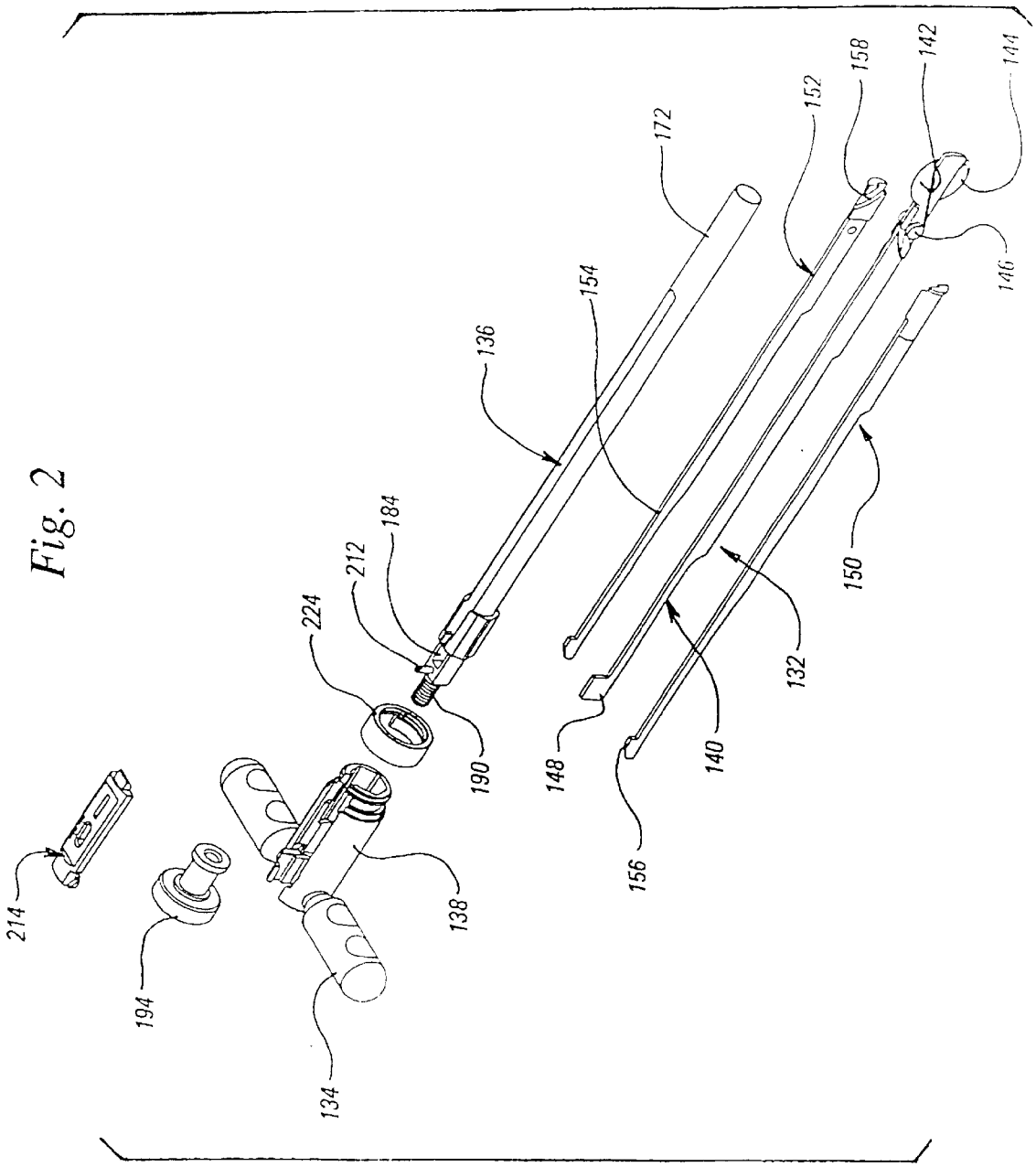
FIG. 2 is an exploded view of the reamer of FIG. 1.
Figure 3:
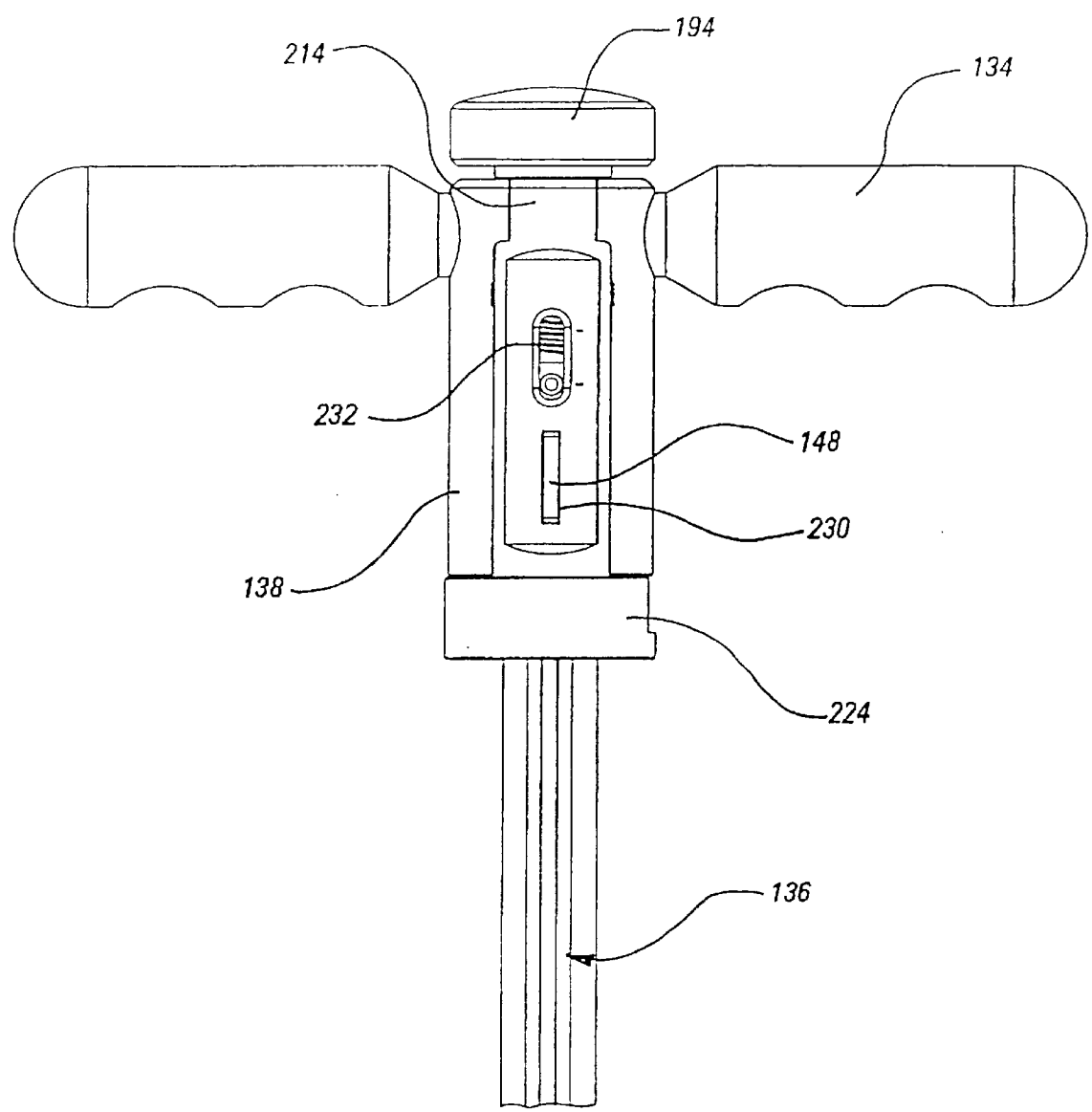
FIG. 3 is top down view of an embodiment of the blade advancer arbor portion of the reamer of FIG. 1.

In FIGS. 1 and 2 an embodiment of the inventive reamer, indicated generally by reference numeral 132, is shown. The reamer 132 includes a handle 134, a blade advancing arbor 138 and a main shaft 136. Within the main shaft is an elongate shaft 140 which may extends distally beyond the distal end of the main shaft 136. As may be seen, the elongated shaft 140 includes a blade advancing tab 148 at the proximal end and a pair of blades 142, 144 hingedly mounted to the distal end by a hinge pin 146.

As may best be seen in FIG. 2, main shaft 136 is hollow to allow it to carry the elongated shaft 140 and the blade guides 150 and 152. The blade guides 150 and 152 each have a relatively slender shaft 154 a proximal tab 156 and an arcuate guide slot 158 at their distal ends. The elongated shaft 140 is positioned between the blade guides 150 and 152.

The diameter of shaft 136 at distal end 172 is sized such that shaft 136 can be inserted into a patient's body with distal end 172 placed against a diseased disc or other bone without shaft 136 having undue interference with other anatomical organs.

Figure 4:
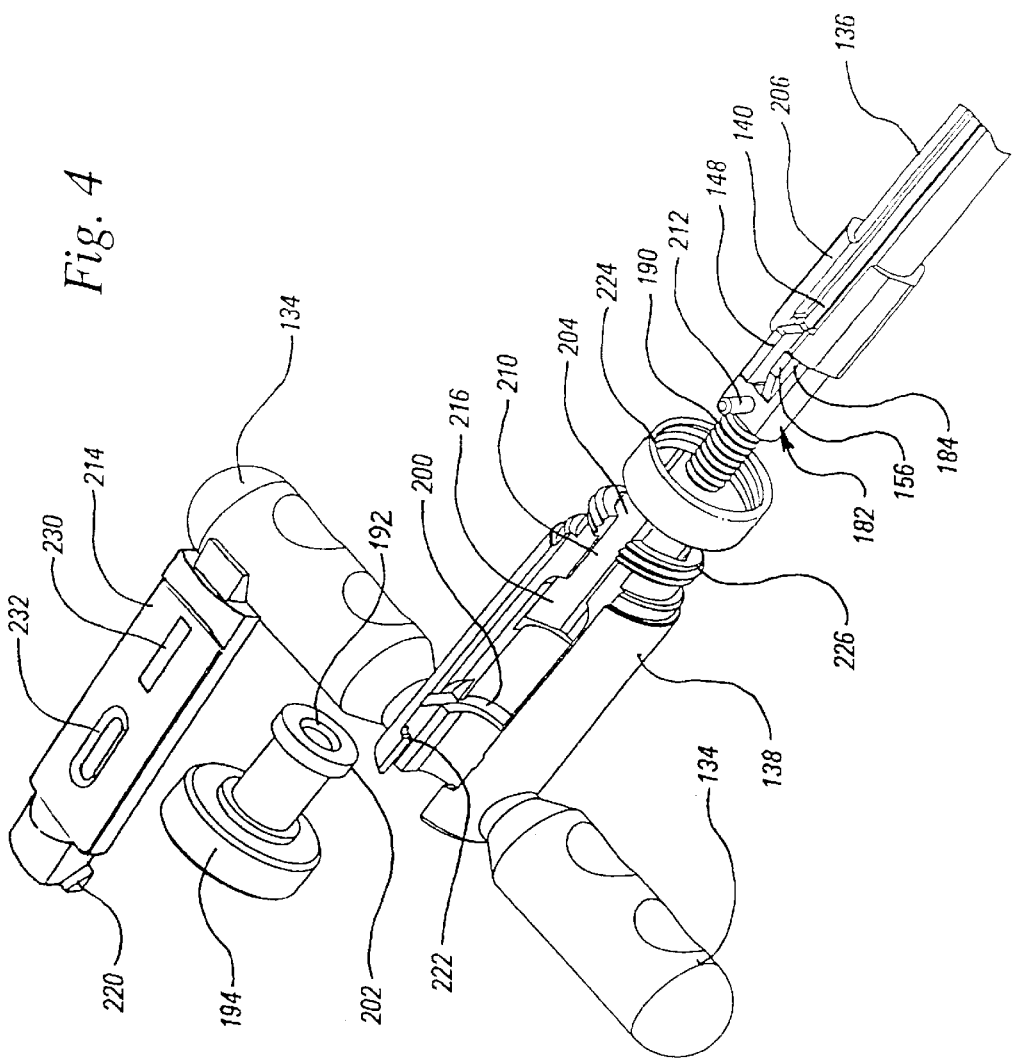
FIG. 4 is an exploded view of an embodiment of the blade advancer arbor.
Figure 5:
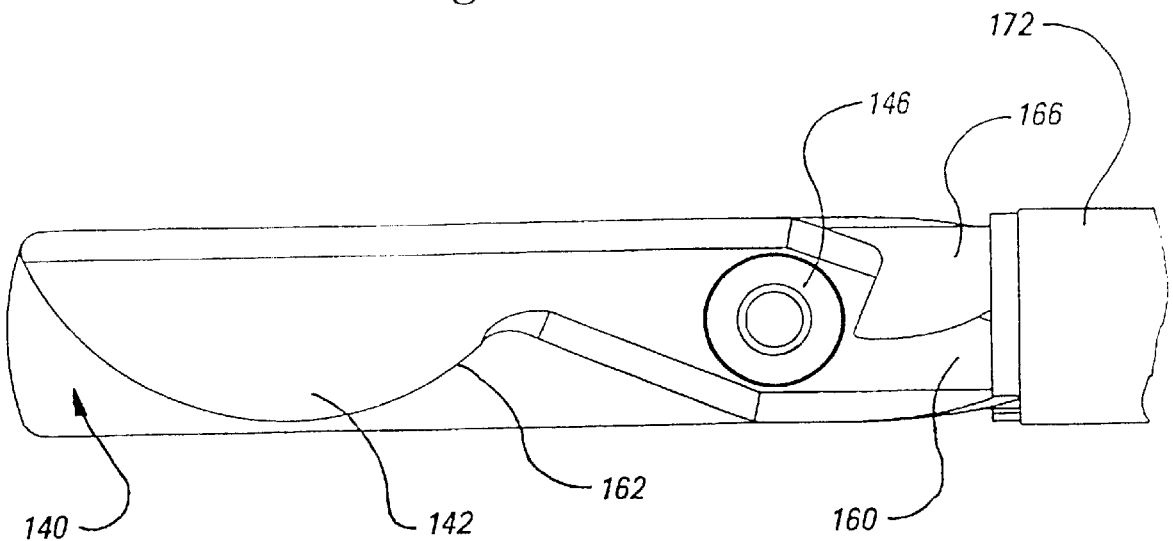
FIG. 5 is a side view of the blade assembly portion of the reamer of FIG. 1, wherein the blades are shown in the retracted position.
Figure 6:
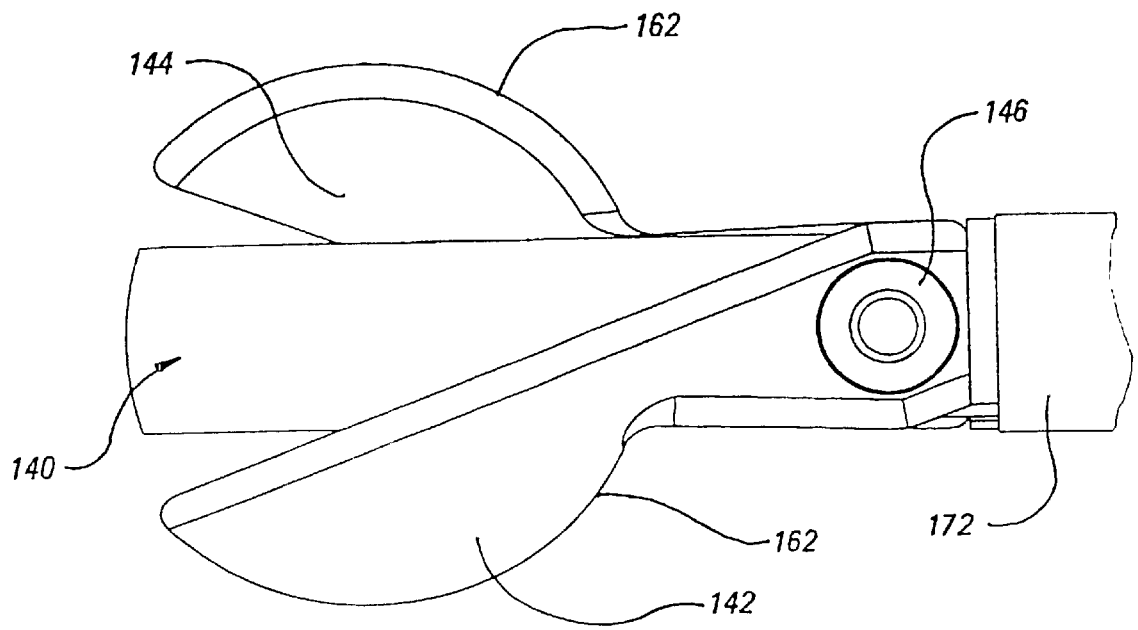
FIG. 6 is a side view of the blade assembly portion of the reamer of FIG. 1, wherein the blades are shown in the retracted position.

FIG. 4 shows that main shaft 136 is attached to a guide member 182 which defines a guide tab slot 184 for engaging the guide tabs 156. The blade advancing tab 148 and the associated shaft 140 longitudinally moveable therebetween.

The end of the guide member 182 includes a threaded shaft 190 which is received into an opening 192 in blade advancer knob 194. The guide member 182 is inserted into an opening in blade advancer barrel 138. Blade advancer barrel 138 includes an annular recess 200 to mate with knob lip 202 which rotatably secures the knob 194 to the barrel 138. The barrel 138 may include a shaped opening 204 designed to engage shaped member 206 on the guide member 182.

In the embodiment shown, the guide member 182 is inserted into opening 204 with the elongated blade shaft 140 and the blade advancing tab 148 as well as blade guides 156 fully inserted into slot 184. The blade advancing tab 148 projects above the guide member 182 such that a groove 210 may be provided in the blade advancer barrel 138 to allow the assembly to pass therewithin.

The guide member 182 may include a pin 212 which passes from the guide member 182 across the barrel opening 216 to engage the pin opening 232 of the slide door 214. When properly assembled the tab 148 protrudes through the tab opening 230 of the door 214 such as may be seen in FIG. 3. This mutually engaging relationship keeps the elongated blade shaft 140 from moving.

After the guide member 182 is inserted fully into the barrel 138, the slide door 214 is placed onto blade advancer barrel 138 to close the access opening 216. The slide door may be held at the proximal end by engagement of its tabs 220 to slots 222 in the barrel. The distal end of the door 214 is held in position by a lock ring 224 that engages with threads 226 or the like on the distal end of barrel 138 as is shown in FIG. 4.

As stated above, the slide door 214 includes a pair of openings 230, 232. Opening 230 engages with tab 148 to keep the elongated shaft 140 from moving. Observation of the position of the pin 212 within the confines of opening 232 allows a user to track the degree of movement that the shaft 136 makes longitudinally in response to turning knob 194.

As may best be seen in FIG. 4, when knob 194 is turned or rotated, the shaft 136 is moved inwardly or outwardly within barrel 138. The movement of the shaft 138 is relative to the elongate shaft 140 which is held stationary by the blade advancing tab 148 within shaft 138. This functional relationship causes the blades 142 and 144 to pivotally retract or expand relative to shaft 136, such as may be seen in FIGS. 5 and 6. However, movement of knob 194 actually causes the entire shaft 136, together with blade guides 150 and 152, which forces the blades to move as their engagement members 160 move within arcuate guide slots 158 of the blade guides.

Figure 7:
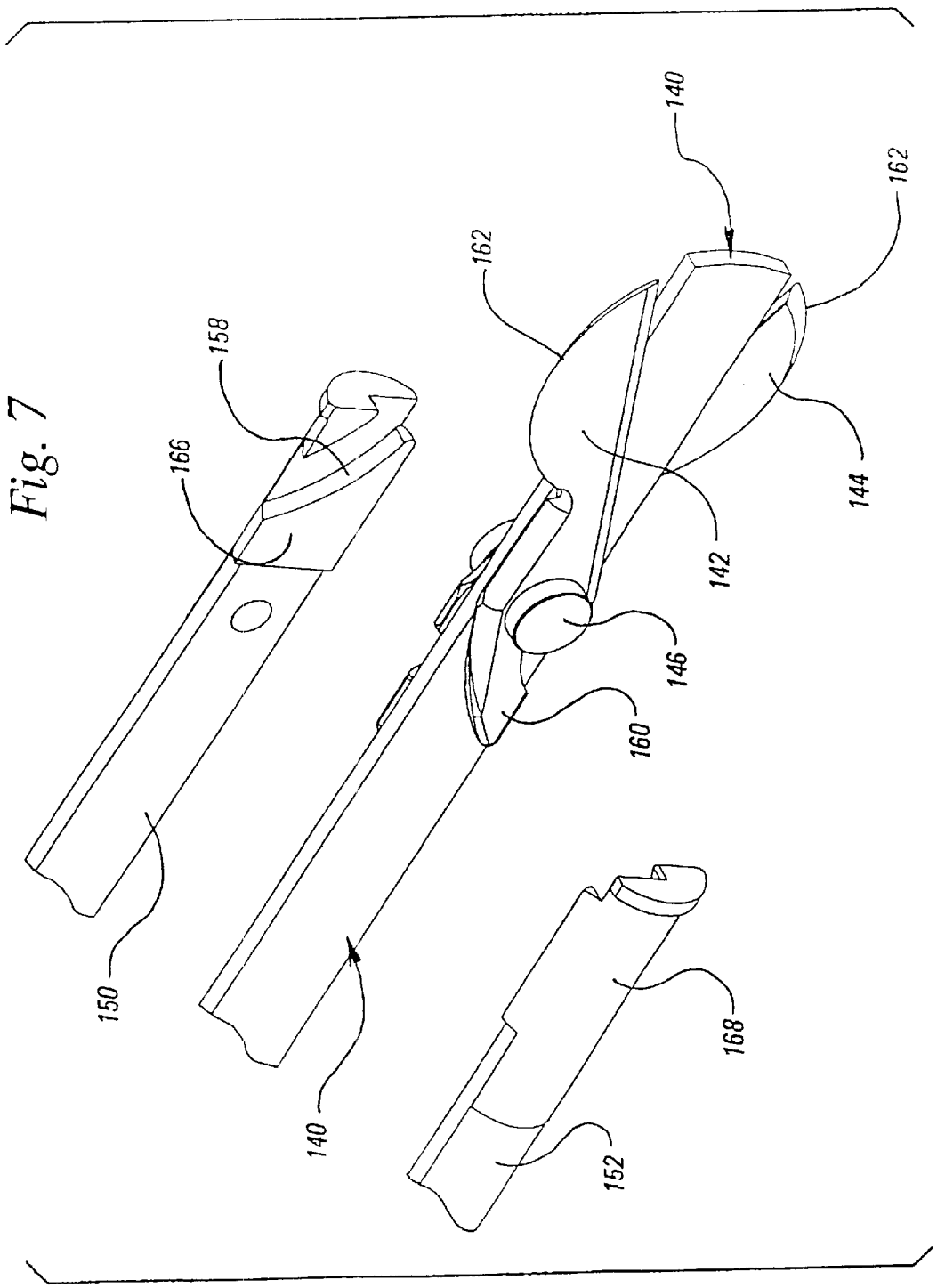
FIG. 7 is an exploded view of an embodiment of the blade assembly and guides.
Figure 8:
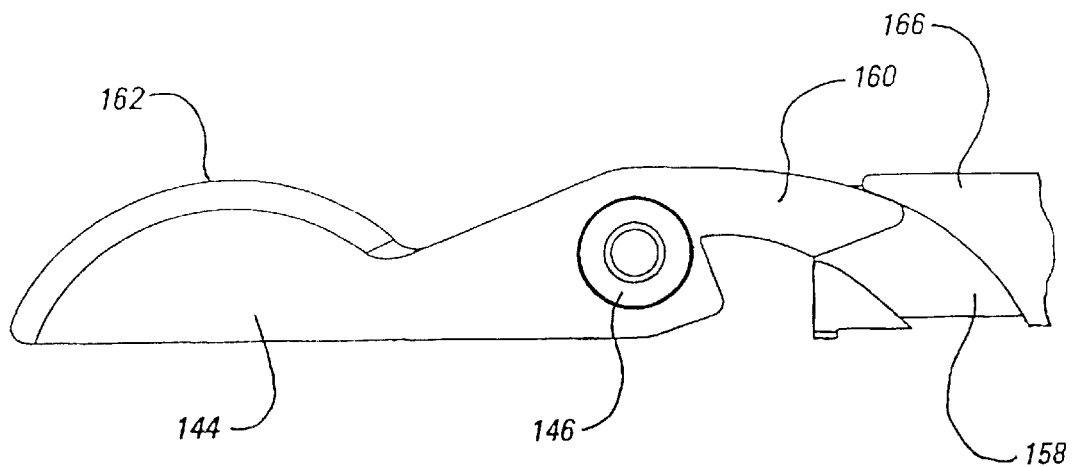
FIG. 8 is an enlarged view of a portion of the distal end of the blade assembly with a blade in the retracted position.
Figure 9:
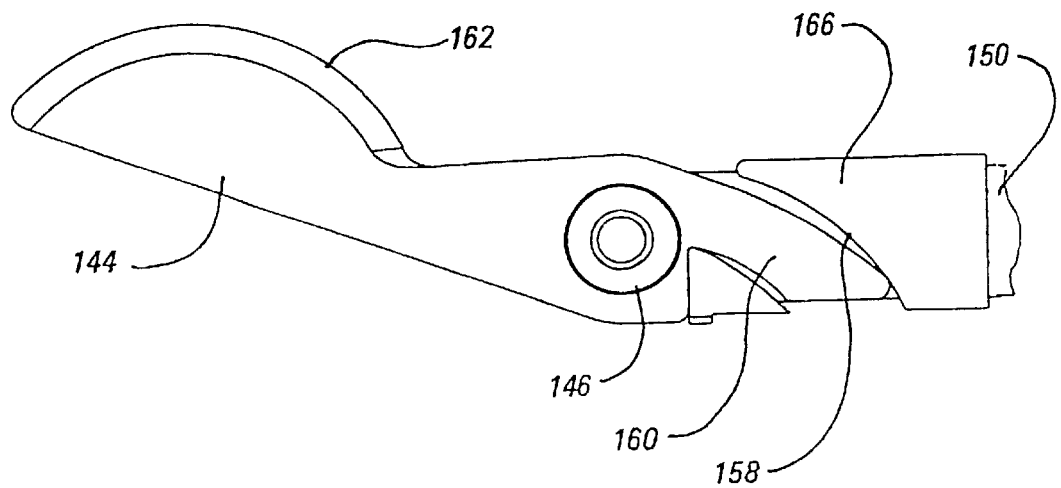
FIG. 9 is an enlarged view of a portion of the distal end of the blade assembly with a blade extended.
Figure 10:
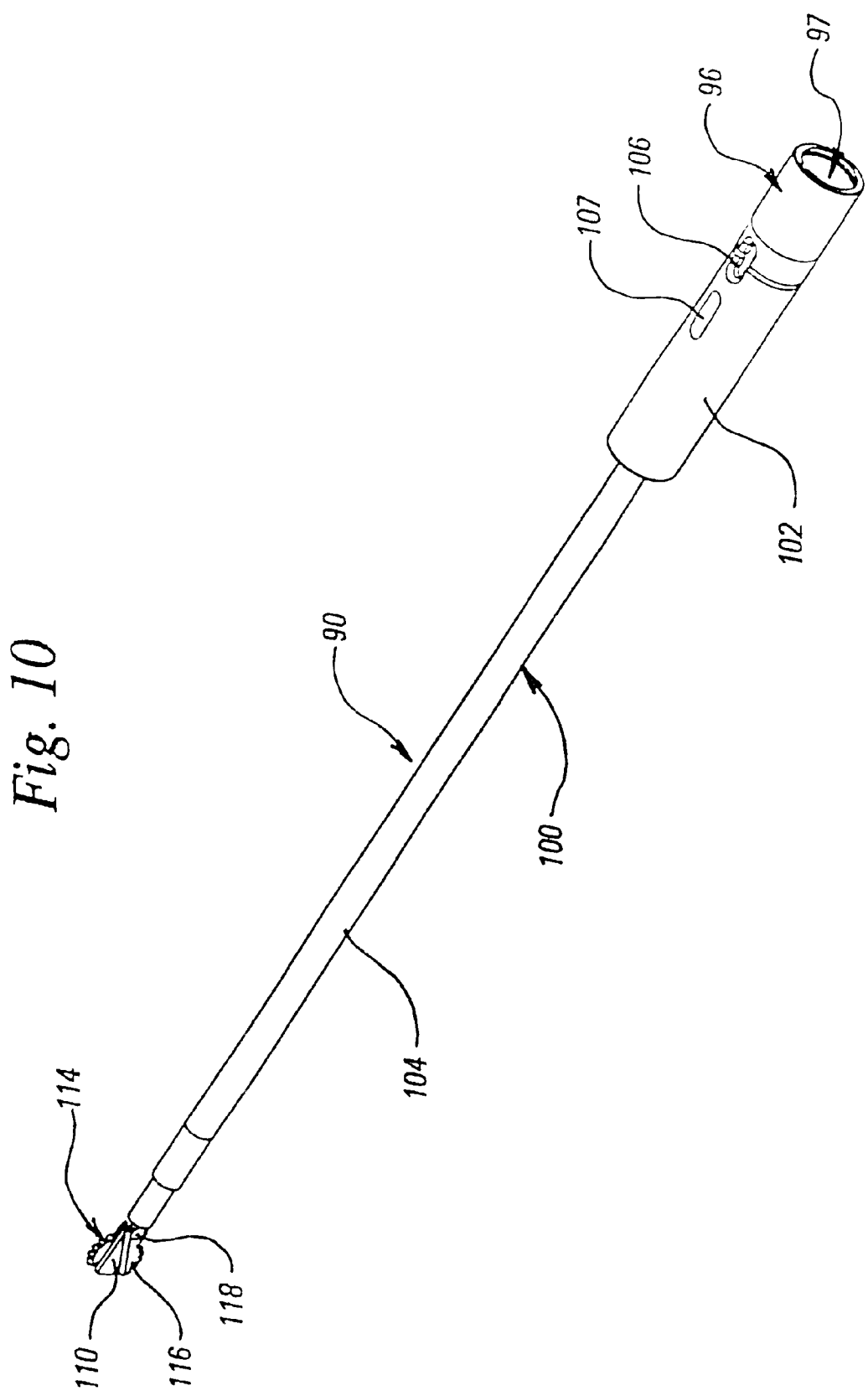
FIG. 10 is a perspective view of an alternative embodiment of the reamer.

As may best be seen in FIG. 7, the blades 142, 144 each include an engagement member 160 which aligns with arcuate guide slot 158, defined by the diverter housings 166 and 168 respectively. When the engagement members 160 are fully within arcuate guide slots 158, the blades are extended out their maximum extent for cutting with blade portions 162, such as may best be seen in FIG. 9. As the engagement members 160 are withdrawn from the guide slots 158, such as may be seen in FIG. 8, the blades 142 and 144 are retracted for insertion and/or withdrawal from the patient.

Turning to FIGS. 10–17, an alternative embodiment of the invention is shown. FIGS. 10–17 are directed to a more compact form of the reamer of the present invention. As depicted herein, the diameter of the reamer 90 with closed blades, such as may best be seen in FIG. 14 may have a diameter of approximately 5 mm or less. The present reamer 90 may be used to create openings through pedicles, channels for anterior cruciate ligaments and the like. Rather, an elongated tube and barrel 100 carry a long rod 92 that attaches at the proximal end to a turn wheel 96 that moves the blades distally and proximally. The end of the long rod 92 is attached to two like blades by a pivot 118 that allows the blades 114 and 116 to change position. Each of the blades 114 and 116 have a sloping lever side 120 that allows them to move smoothly outwardly. A notch or stop 126 bottoms out against the main tube 100 to prevent further movement. The handle may have a flat slot 107 milled therein that allows the user to see whether the rod 92 is in position for cutting or pushed forward for no cutting. A second slot 106 provides an access space sufficient to allow a user to remove the retaining clip 108, so that the reamer may be disassembled as discussed below.

Note that if the blades 114 and 116 were ever stuck in an open position, the handle 96 could be removed, allowing the tube to be removed and then the blades 114 and 116 would have nothing to keep them open. This blade setup allows disassembly if the blades are stuck open in the bone. Prior reamer designs may be difficult to disengage in such an event. In this design, the entire device may be disassembled from the proximal end such that the parts are released allowing the blades 114 and 116 to pivot freely. In the embodiment shown in FIG. 11, removal of the retaining clip 108 will allow the turn wheel 96 to be separated from the barrel 102. The barrel 102 along with the shaft housing 104 may then be slid off of the elongate shaft 92. When the shaft 92 is no longer retained by the housing 104, the blades 114 and 116 will be free to move into the retracted position by merely pulling the shaft 92 from the bone or operation site (not shown).

As shown in FIGS. 10–14, reamer 90 is elegantly simple. It includes an elongated shaft 92 with a proximal tab 129 which may include a threaded proximal end 94 which may receive the tab 129 via slot 128. The combined threaded proximal end 94 and elongate shaft 92 is engaged with the turn wheel 96 thereby providing a the shaft 92 with the ability to be moved up and down within holder 100 as the wheel 96 is turned.

The holder 100 includes an enlarged barrel 102 into which the turn wheel 96 may partially descend and a lower hollow cylindrical guide 104. The distal end 110 of shaft 92 includes a narrow tang 111 which has an opening therethrough to allow blades 114, 116 to be hingedly attached via a hinge pin member 118.

Figure 14:
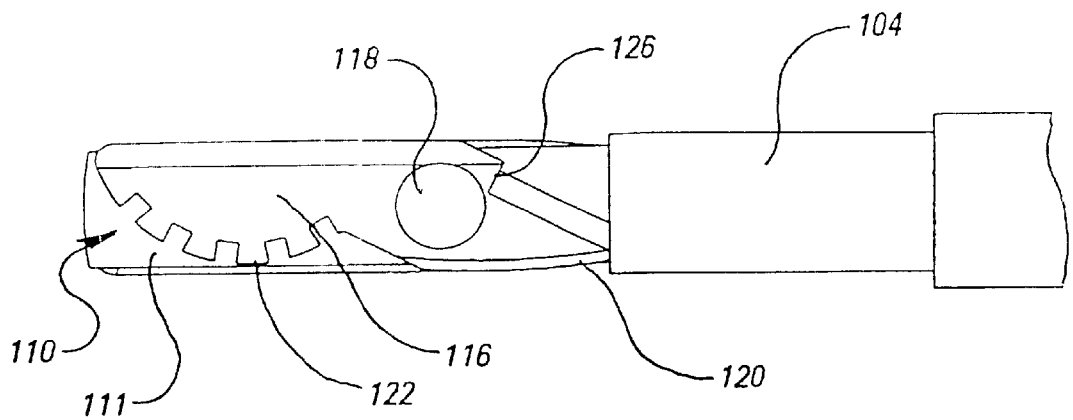
FIG. 14 is a side view of an alternative embodiment of the blade assembly wherein the blades are retracted.
Figure 15:
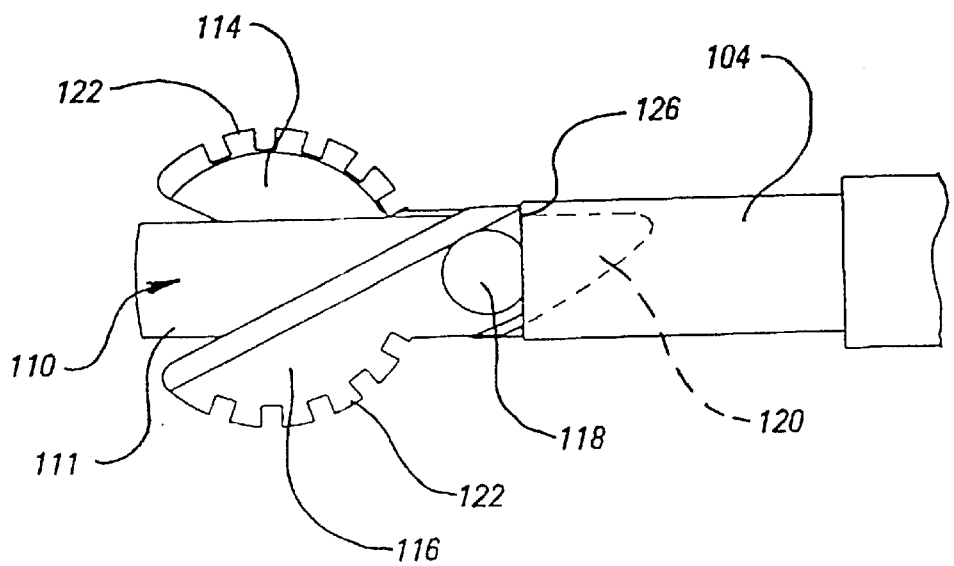
FIG. 15 is a side view of the blade assembly shown in FIG. 14 wherein the blades are extended.

As best shown in FIGS. 14 and 15, the blades 114, 116 include a ramp portion 120 sized to enter cylindrical tube 104 and a cutting portion 122. As may be seen in FIGS. 14–17, the cutting portion 122 of the blades 114 and 116 may be serrated. When turn wheel 96 is turned to pull the shaft 92 up into the cylindrical tube 104, the ramped portion 120 enters the tube 104 and begins to extend the blade portion 122 out past the diameter of the tang 111. As shown in FIG. 15, blades 114, 116 are at their most extended portion as limited by a stop member 126 which abuts against the cylindrical tube 104 preventing further extension.

Turn wheel 96 may include depth marking slot 107 which allows the user to see how far the blades have extended or retracted. In addition, the portion of the shaft 92 which may be seen through the slot 107 may have visible markings or surface features to better provide a visual basis for determining the extent of the blade retraction or extension based on the relative position of the shaft 92 within the slot 107. In the unlikely event that the reamer blades 114, 116 cannot be readily retracted within the cavity being formed, the turn wheel 96 may be removed, allowing the holder 100 to slide away from the shaft 92. In such a case, the blades 114, 116 would freely pivot on hinge pin 118 allowing the remainder of the reamer 90 to be readily removed.

Figure 11:
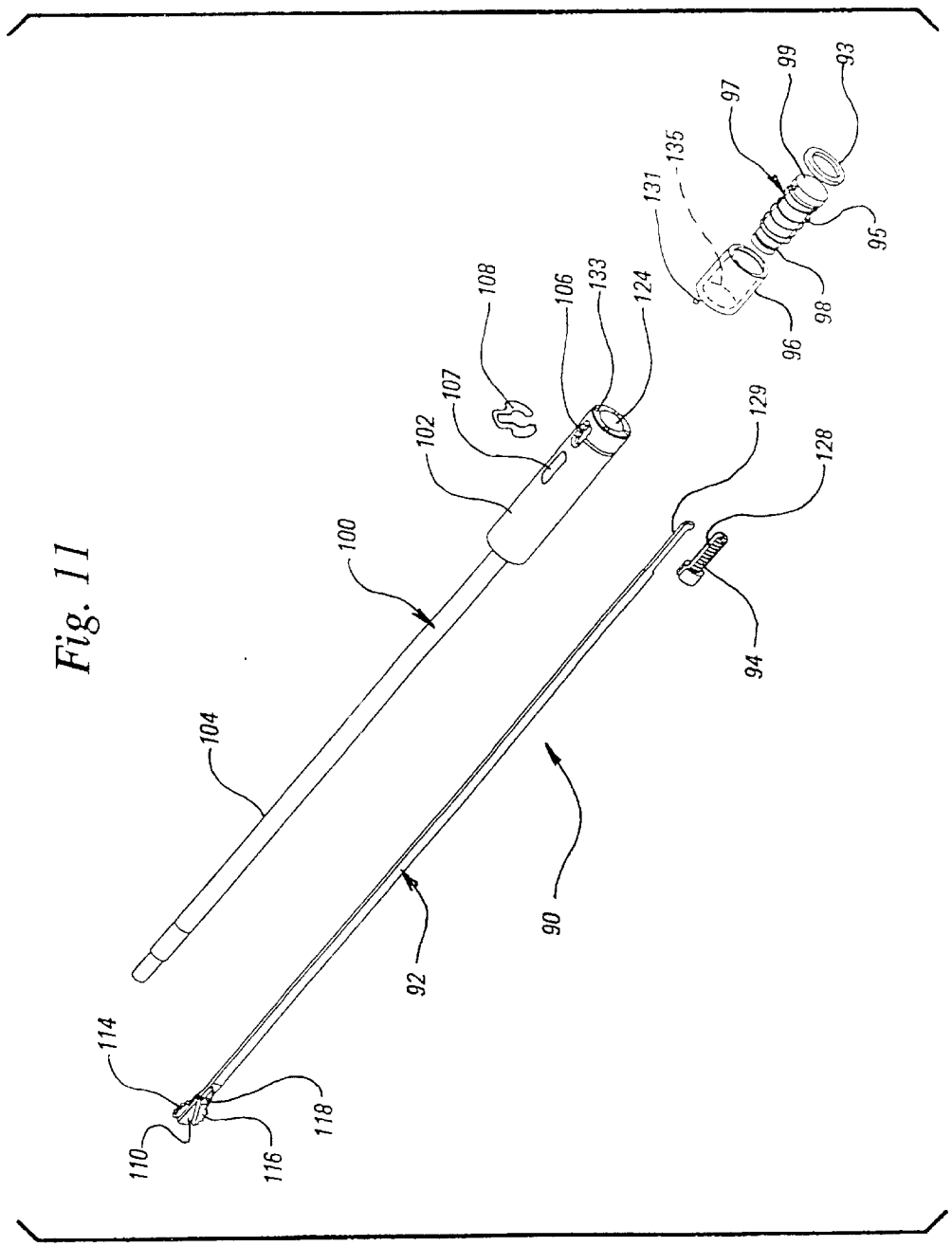
FIG. 11 is an exploded view of the reamer of FIG. 10.

FIGS. 11–13 show the construction of the barrel 102 and the interface of the turn wheel 96 to the reamer 90. Turn wheel 96 includes a projection member 97, which may be a threaded nut or screw which is inserted into the turn wheel 96 and threadingly engaged to a retaining clip 108. The retaining clip 108 is fittingly or frictionally engaged to a retaining slot 109 positioned about the proximal end of the barrel 102, the position of the retaining slot 109 corresponds to the position of the indentation 98 of member 97 when member 97 is threadingly engaged to threaded proximal end 94. The slot 109 has a diameter less than the diameter of the surrounding barrel 102. Barrel 102 includes a bore which communicates through the cylindrical tube 104.

As may be best understood from viewing FIG. 11, in order for the turn wheel 96 to be properly engaged to the barrel 102 a variety of components must initially be assembled with in the wheel 96. A projecting member 97 is inserted through the turn wheel 96. Disposed about the projection member 97 is a biasing member such as a coiled spring 95. The spring 95 is pushed into the wheel 96 along with the member 97. A retaining ring 93 is fittingly engaged into the wheel 96 to retain the member 97 and spring 95 therein.

As may best be seen in FIG. 13, at the proximal end of the barrel 102, an opening 124 is formed which conforms to the cross-sectional shape of the threaded end 94 and tab 129. The indentation 98 of the projection member 97 engages the retaining clip 108 such that when threaded end 128 is threaded into opening 130 or the turn wheel 96, the turn wheel 96 cannot be removed from shaft 92 without unscrewing the shaft 92 from opening 130 and removing lock pin 108.

In one embodiment of the invention, when the turn wheel 96 is assembled in the manner described above, the spring 95 (shown in FIG. 11) is biased between shoulder 99 of member 98 and shoulder 135 of the turn wheel 96. This biasing relationship provides sufficient tension force to between the member 98 and the wheel 96 to prevent unintentional movement of the turn wheel relative to the barrel 102. In order to rotate the wheel 96, the wheel 96 must be pulled longitudinally away from the barrel 102 with sufficient force to overcome the biasing force of the spring 95. When pulled in this manner the wheel may be freely rotated.

In an alternative embodiment of the invention, the turn wheel includes a plurality of engagement pins 131. Each engagement pins 131 is engaged to receiving holes 133. In order to rotate the wheel 96 the wheel 96 is pulled in the manner described above, but additionally must be pulled a sufficient distance away from the barrel 102 to disengage the pins 131 from the holes 133. The wheel 96 may then be rotated to a point where the pins 131 may be reinserted into the holes 133 in an advancing clockwise or counter-clockwise manner.

When the reamer 90 is assembled in the manner described above, clockwise rotation of the turn wheel 96 causes shaft 92 to be pulled up tube 104 such that ramp portion 120, such as may be seen in FIGS. 14–17, enters tube 104 causing the blades 114, 116 to extend outwardly until the stop 126 abuts with the distal end of tube 104.

As shown in FIG. 14–17, blades 114 and 116 include a cutting edges 122. In the embodiment shown, the cutting edges 122 may be serrated, however straight, or curved cutting edges 122 may also be provided. In the various embodiments described herein, the blades of the inventive reamer may be constructed from a variety of materials such as metal, composite materials such as carbon etc. Where the blades are metal, the metal may be any type of metal suitable for use in constructing a blade for use in medical procedures. Such metals may include: stainless steel, spring steel, titanium, nickel, or any alloys thereof.

As may be seen in FIG. 14, the blades 116 (114 is not shown) are shown in a mostly retracted position, whereas in FIG. 15 the blades 114 and 116 are depicted in a fully extended position. Any position between a fully retracted and fully extended position is possible with the reamer tool 90 of the invention.

In operation, the blades 114 and 116 are fully retracted and the device 90 is inserted into an opening drilled into the body material where a cavity is to be formed. Typically a hole is drilled into the vertebral body or other bone or area that needs to be reamed to a diameter larger than the outside drill hole. The hole is drilled in the bone, and then a guide tube may be abutted against the bone and adjusted to the proper length or depth where it is desired to ream the hole. The reamer 90 is then inserted through the optional guide tube with the blades 114 and 116 in the retracted position, such as is shown in FIG. 14. Once inserted into the bone to a desired depth, the turn wheel 96 is rotated to begin expansion of the blades 114 and 116. Rotation of the reamer 92 with the blades 114 and 116 gradually expanding, provides a cutting action which reams out a chamber from within the bone.

Figure 16:
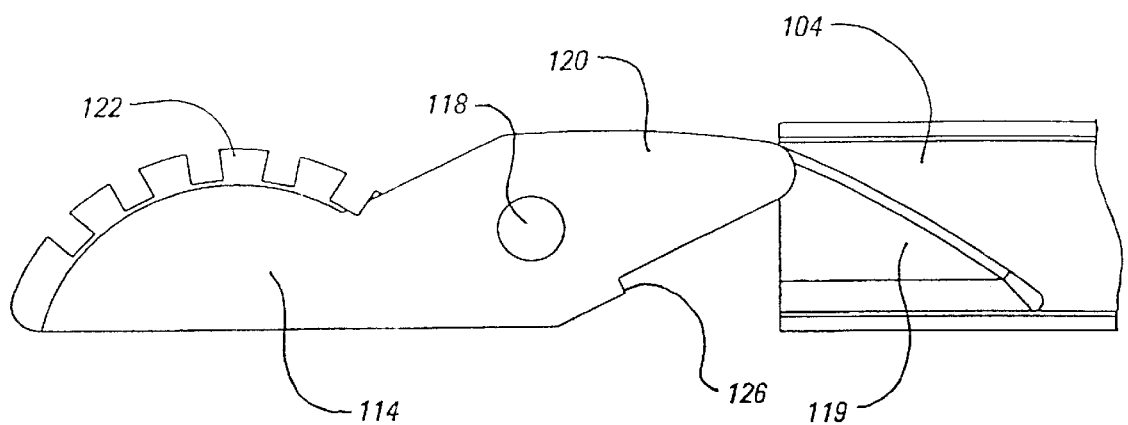
FIG. 16 is an enlarged view of a portion of the distal end of the blade assembly of FIG. 14 with a blade in the retracted position.
Figure 17:
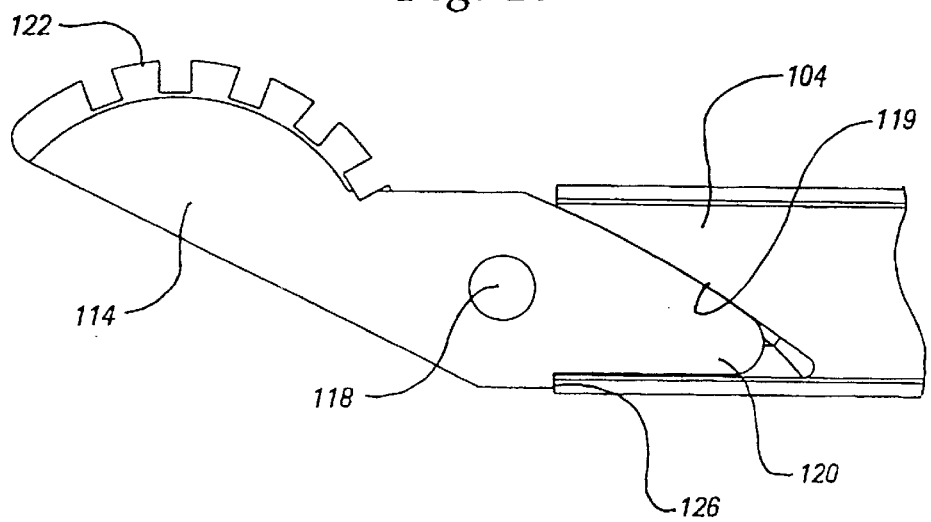
FIG. 17 is an enlarged view of a portion of the distal end of the blade assembly of FIG. 14 with a blade extended.

In use, turning or rotating the turn wheel 96 relative to the barrel 102 causes the shaft 92 to be moved longitudinally relative to the shaft housing 104. This action causes the blades 114 and 116 to pivot around the pivot member 118 thereby expanding out from or retracting into the tapered ramps 119, as seen in FIGS. 16 and 17, depending on the direction of the turn wheel's rotation. As the blades 114 and 116 are rotated out of the ramps 119 the entire reamer 92 may be rotated causing the blades 114 and 116 to cut an expanding hole in the cavity, which is limited in size to the maximum expanded state of the blades 114 and 116, such as is shown in FIG. 15.

Once a reamed cavity is made, the blades 114 and 116 are retracted by rotating the turn wheel 96 in a direction opposite that which was used to expand the blades, until the blades 114 and 116 are fully retracted. However, it should be noted that unlike in the embodiment shown in FIGS. 1–9, the present embodiment does not rely on the ramps or slots to retract the blades. Instead, the blades 114 and 116 may be free to retract when pulled from the hole. Thus when the reamer 90 is withdrawn from the hole the blades 114 and 116 may retract by themselves as a result of engagement with the drill hole shaft or the guide tube.

The surgeon may visualize the degree the blades 114 and 116 extend by viewing the position of the shaft 92 relative to the barrel 102, through view port 107. The shaft 92 may have markings or surface features to make such position determinations easier. In the embodiment shown, the surgeon can see how far down the shaft 92 moves as the turning wheel 96 is rotated. The reamer 90 may be calibrated to show the distance the blades project from the tool.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. An expandable reamer comprising:
   a) an elongated hollow shaft having a proximal and a distal end, the distal end being closed and having a pair of opposing side openings adjacent the closed end;
   b) a pair of internal blade members within said hollow shaft;
   c) a mechanism for moving said blades from a retracted position within the shaft to a cutting, extended position through said side openings.

2. The expandable reamer of claim 1 wherein said distal closed end includes an inner, centrally located wedge constructed and arranged to direct the internal blade members out of said side openings when pressed distally.

3. The expandable reamer of claim 2 wherein said internal blade members each include an elongated shaft having a distal and a proximal end, said proximal end extending up to said blade moving mechanism and a cutting blade on a distal end of said elongated shaft which are completely within said hollow shaft until said elongated shafts are urged distally by said blade moving mechanism.

4. The expandable reamer of claim 3 wherein said blade moving mechanism is constructed and arranged to engage said proximal end of said blade member elongated shaft and simultaneously move both blades distally or proximally in response to operator movement of said blade moving mechanism.

5. The expandable reamer of claim 4 wherein said blade moving mechanism includes an adjusting screw which when rotated causes said blades to move distally or proximally in said elongated hollow tube in response to the direction of rotation and degree of rotation.

6. The expandable reamer of claim 5 further including an indicator mechanism toward the proximal end of said reamer which is visible from the outside of said reamer and shows relative movement of said blades proximally and distally within said hollow shaft to indicate position of the cutting blades.

7. The expandable reamer of claim 6 wherein said reamer includes a mechanism for applying rotational torque to said hollow shaft such that said cutting blades rotate and provide a cutting operation.

8. The expandable reamer of claim 7 wherein said cutting blades are constructed and arranged to fully retract within said hollow shaft until said blade moving mechanism urges them out said side openings such that said cutting blades are not in a cutting position until desired.

9. The expandable reamer of claim 8 wherein said elongated shafts of said blade members are rectangular in cross-section and abut against each other within said hollow shaft to increase torsional rigidity.

10. The expandable reamer of claim 9 wherein the proximal ends of said elongated shafts of said blade members include notches which engage with an adjustment slide of said blade moving mechanism.

11. The expandable reamer of claim 10 wherein said adjustment slide is inserted through a side access port which is covered by a locking cover.

12. The expandable reamer of claim 11 wherein said blade members are spring steel and constructed and arranged to have a slip fit within the hollow shaft such that the blade members may be inserted into said hollow shaft through said side openings while limiting movement of said blade members within said shaft.

13. An expandable reamer comprising:
   a) an elongated shaft having a proximal end and a distal end, a pair of blade members pivotally engaged to the distal end of the elongated shaft, a pair of elongated blade guides positioned immediately adjacent to the elongate shaft, the elongate blade guides each having a guide slot, at least a portion of each of the pair of blade members being operatively engaged to one of the guide slots;
   b) an elongate hollow tube, the elongate hollow tube being disposed substantially about the elongated shaft and the pair of elongated blade guides, the elongate hollow tube being longitudinally moveable relative to the elongated shaft;
   c) a handle, the handle having a hollow engagement barrel and at least one griping member extending therefrom, the hollow engagement barrel having a first end engaged to the elongate hollow tube, and a second end having a control knob, the control knob being operatively engaged to the elongate hollow tube, whereby when the control knob is rotated the elongate hollow tube is moved longitudinally relative to the elongated shaft causing the pair of blade members to move between a retracted position and an extended position.

14. An expandable reamer comprising:
   a) an elongated shaft having a proximal end and a distal end, a pair of blade members being pivotally engaged to the distal end of the elongated shaft, the distal end of the elongate shaft having a pair of blade slots constructed and arranged to slidingly and removably receive at least a portion of one of the blade members:
   b) an elongate hollow tube, the elongate hollow tube being disposed substantially about the elongated shaft, the elongated shaft being longitudinally moveable relative to the elongate hollow tube;
   c) a turn wheel, the turn wheel operatively engaged to the proximal end of the elongated shaft and positioned proximal to the elongate hollow tube, whereby when the turn wheel is rotated the elongated shaft is moved longitudinally relative to the elongate hollow tube causing the pair of blade members to move between a retracted position and an extended position.

* * * * *